United States Patent
Hsiao et al.

(10) Patent No.: US 6,903,235 B2
(45) Date of Patent: Jun. 7, 2005

(54) PHARMACEUTICAL-GRADE FERRIC CITRATE

(75) Inventors: Yih-Ming Hsiao, Commack, NY (US);
Hsueh-Hung Chiu, Tau Yuan (TW);
Hsiu-Ching Wang, Tau Yuan (TW);
Yu-Chen Chang, Tau Yuan (TW)

(73) Assignee: Panion & BF Biotech Inc., Taipei (TW)

( * ) Notice: Subject to any disclaimer, the term of this patent is extended or adjusted under 35 U.S.C. 154(b) by 0 days.

(21) Appl. No.: 10/682,045

(22) Filed: Oct. 8, 2003

(65) Prior Publication Data

US 2005/0080283 A1 Apr. 14, 2005

(51) Int. Cl.$^7$ .......................... C07C 55/22; C07C 51/42; A61K 31/295
(52) U.S. Cl. ..................... 562/593; 562/594; 514/502
(58) Field of Search .................................. 562/594, 593

(56) References Cited

U.S. PATENT DOCUMENTS 5,753,706 A    5/1998    Hsu ........................... 514/578

OTHER PUBLICATIONS

Chem. Abstracts, vol. 55, No. 3 (Feb. 6, 1961), Abstract Only, Abstract # 3939d (Of USSR Patent No. 129,194).*

WPIDS Abstract Only, JP 2003183217 (KAWA–N), 2003.*

Biosis Abstract Only, Gutteridge, Free Radical Biology and Medicine, (1991), vol. 11, No. 4, pp. 401–406.*

Webster's II New Riverside University Dictionary, published 1984 by Riverside Publishing Company (p. 763).*

* cited by examiner

*Primary Examiner*—Raymond J. Henley, III
(74) *Attorney, Agent, or Firm*—Dellett & Walters

(57) ABSTRACT

The present invention relates to pharmaceutical-grade ferric citrate. Pharmaceutical-grade ferric citrate contains a definite composition and a definite hydrate. The present invention also relates to a method using a solid—solid reaction to produce pharmaceutical-grade ferric citrate. The present invention also relates to a pharmaceutical composition comprising a therapeutically effective amount of pharmaceutical-grade ferric citrate and a food comprising pharmaceutical-grade ferric citrate.

8 Claims, No Drawings

PHARMACEUTICAL-GRADE FERRIC CITRATE

BACKGROUND OF THE INVENTION

1. Field of the Invention

The present invention generally relates to pharmaceutical-grade ferric citrate, and particularly to a pharmaceutical composition, food comprising pharmaceutical-grade ferric citrate and a method for manufacturing pharmaceutical-grade ferric citrate.

2. Description of Related Art

U.S. Pat. No. 5,753,706 ('706) discloses that a ferric citrate compound can be used to control phosphate metabolism and prevent metabolic acidosis in patients. A ferric citrate compound is used with patients suffering from renal failure associated with hyperphosphatemia or patients predisposed to development of a hyperphosphatemic condition. Ferric citrate is used as a food supplement, too. According to the '706 patent, ferric citrate was purchased from the Sigma-Aldrich Company, contained 16.5%–18.5% of Iron (III) and had a formula of $FeC_6H_5O_7$ and a formula weight of 244.9. Ferric citrate is garnet-red, transparent scales or pale-brown powder, odorless and slightly ferruginous tasting. Ferric citrate is slowly but completely soluble in cold water and readily soluble in hot water but diminishes in solubility with age (The Merck Index, $12^{th}$ Edition, page 4068).

Although ferric citrate is commercially available, the purchased ferric citrate is a combination of iron and citric acid of indefinite composition (The Merck Index, $12^{th}$ Edition, page 4068) probably because of the difficulty encountered in its preparation. People knowledgeable in the art understand and necessarily accept that commercially available ferric citrate contains different molar ratios of iron and citric acid and also contains different amounts of hydrate.

SUMMARY OF THE INVENTION

The first objective of the present invention is to provide pharmaceutical-grade ferric citrate having ferric citrate with a definite hydrate where pharmaceutical-grade ferric citrate has the empirical formula $FeC_6H_5O_7.3.5H_2O$.

A second objective of the present invention is to provide a method for manufacturing pharmaceutical-grade ferric citrate. The method comprises:

mixing solid citric acid and a solid ferric salt to form a mixture;

adding alcohol to the mixture; and filtering the mixture to obtain solid pharmaceutical-grade ferric citrate.

The third objective of the present invention is to provide a pharmaceutical composition comprising a therapeutically effective amount of pharmaceutical-grade ferric citrate and a pharmaceutically acceptable carrier, excipient or diluent. The pharmaceutical composition can provide iron to animals. The pharmaceutical composition can be used but is not limited for treatment of iron-deficiency diseases, renal failure and hyperphosphatemia.

The fourth objective of the present invention is to provide food comprising pharmaceutical-grade ferric citrate.

Further benefits and advantages of the present invention will become apparent after a careful reading of the detailed description.

DETAILED DESCRIPTION OF THE INVENTION

Pharmaceutical-grade ferric citrate in accordance with the present invention is of the empirical formula $FeC_6H_5O_7.3.5H_2O$. Pharmaceutical-grade ferric citrate contains ferric citrate with a definite hydrate.

Ferric citrate can be produced by the reaction of a ferric salt with citric acid. To make pharmaceutical-grade ferric citrate, the synthesis process should have less than three distinct steps to make the product's composition easier to control. A method for manufacturing pharmaceutical-grade ferric citrate in accordance with the present invention comprises the following steps:

mixing solid citric acid and a solid ferric salt to form a mixture;

adding alcohol to the mixture; and filtering the mixture to obtain solid pharmaceutical-grade ferric citrate.

Preferably, the method for manufacturing pharmaceutical-grade ferric citrate further comprises drying solid pharmaceutical-grade ferric citrate obtained drying by heat. More preferably, obtained solid pharmaceutical-grade ferric citrate is dried at 30° C. to 120° C.

Preferably, the method for manufacturing pharmaceutical-grade ferric citrate further comprises purifying solid pharmaceutical-grade ferric citrate. Obtained solid pharmaceutical-grade ferric citrate may be mixed with alcohol and filtered the mixture one or more times to remove residual quantities of solid ferric salt, citric acid and by-products to improve the purity of solid pharmaceutical-grade ferric citrate.

Preferably, the method for manufacturing pharmaceutical-grade ferric citrate further comprises drying solid pharmaceutical-grade ferric citrate purified by heat after purifying. More preferably, purified solid pharmaceutical-grade ferric citrate is dried at 30° C. to 120° C.

Preferably, the ferric salt is ferric chloride, ferric sulfate or ferric nitrate. More preferably, the citric acid is citric acid monohydrate and the ferric salt is ferric nitrate nonahydrate.

A pharmaceutical composition according to the present invention comprises a therapeutically effective amount of pharmaceutical-grade ferric citrate and a pharmaceutically acceptable carrier, excipient or diluent.

The pharmaceutical composition provides iron to animals. Preferably, the pharmaceutical composition is used for the treatment of iron-deficiency diseases, renal failure and hyperphosphatemia.

A food in accordance with the present invention comprises pharmaceutical-grade ferric citrate.

All of the documents or publications recited in the text are incorporated herein by reference.

Further details of this invention are illustrated in the following examples.

EXAMPLE 1

Preparation of Ferric Citrate 1.1. Ferric Chloride Nonahydrate and Citric Acid were Used to Prepare Ferric Citrate 1.1.1. Method 210.15 g of citric acid monohydrate was placed into a glass reactor.

404.02 g of ferric nitrate nonahydrate was added to the reactor that was in a water bath and mixed for 4 hours.

250 ml of alcohol was added to the reactor and mixed.

The mixture was filtered and solid ferric citrate was obtained.

250 ml of alcohol was added to solid ferric citrate.

The mixture was filtered, and a solid was obtained.

The obtained solid was dried overnight in an oven at 60° C.

Yield 54%.

1.1.2. Analysis

Fe in $FeC_6H_5O_7$ product calculated is 17.62%.

Fe in the $FeC_6H_5O_7$ product measured is 17.56%.

The decomposed temperature of the $FeC_6H_5O_7$ product was 187–191° C.

1.1.3. Stability of the Product

| | Temperature 40° C. ± 2° C. Humidity 75% ± 5% RH | |
|---|---|---|
| Time | Ferric citrate assay | Ferric assay |
| Limited range | 90–110% | 16.5–18.5% |
| Initial | 99.70% | 17.69% |
| 1st month | 99.65% | 17.68% |
| 2nd month | 99.58% | 17.66% |
| 3rd month | 99.79% | 17.70% |
| 6th month | 100.37% | 17.81% |

1.2. Ferric Chloride Hexahydrate and Citric Acid were Used to Prepare Ferric Citrate Ferric chloride hexahydrate is brownish-yellow or orange monoclinic crystals. The ferric chloride hexahydrate has a melting point of about 37° C. and is very hygroscopic and readily soluble in water, alcohol, acetone and ether (The Merck Index, 12$^{th}$ Edition, page 4068).

Ferric chloride hexahydrate and citric acid monohydrate in a 1:1 mole ratio were placed and mixed in an Erlenmeyer flask, then added an aqueous alcohol solution in the Erlenmeyer flask and mixed for one hour. The solution was evaporated to about 10 milliliters. Then the residual solution in the flask was placed in a refrigerator and crystallized.

At the beginning, transparent, needle crystals were formed in the crystallization process. However, the crystal was liquidized in high humidity (about 50% RH at room temperature).

1.3. Ferric Sulfate and Citric Acid were Used to Prepare Ferric Citrate

Ferric sulfate is grayish-white powder, or rhombic or rhombohedral crystals. Ferric sulfate is very hygroscopic, slowly soluble in water, sparingly soluble in alcohol and practically insoluble in acetone and ethyl acetate. Commercial ferric sulfate usually contains about 20% water and is yellowish in color (The Merck Index, 12$^{th}$ Edition, page 4069).

The reaction of ferric sulfate and citric acid exhibited the same phenomena in the reaction of ferric chloride and citric acid.

1.4. Ferric Nitrate Nonahydrate and Citric Acid were Used to Prepare Ferric Citrate Ferric nitrate nonahydrate is pale-violet to grayish-white, somewhat deliquesce crystals. Ferric nitrate is freely soluble in water, alcohol and acetone and slightly soluble in cold concentrated nitric acid. The melting point of ferric nitrate is 47° C. (The Merck Index, 12$^{th}$ edition, page 4069).

The solid—solid reaction of ferric nitrate and citric acid was carried out with a 1:1 mole ratio for 4 hours and formed ferric citrate crystals. Alcohol was added to wash and purify the ferric citrate crystal. Then the mixture was filtered and the solid obtained was dried at 60° C.

EXAMPLE 2

Assay for Iron(III) and Ferric Citrate 0.5 g of ferric citrate, accurately weighed, in 100 mL of water and 5 mL of hydrochloric acid were added in a flask on a water bath until dissolved. 3 g of potassium iodide and 5 mL of hydrochloric acid were added to the flask to form a mixture, and a stopper was inserted in the flask. The mixture was allowed to stand for 15 minutes, and the librated iodine was titrated with 0.1 N sodium thiosulfate solution using a starch test solution as an indicator. A blank test was performed with the same quantities of reagents and in the same manner, and corrections were made if necessary. Each milliliter of 0.1 N sodium thiosulfate is equivalent to 24.496 mg of $FeC_6H_5O_7$ and each milliliter of 0.1 N sodium thiosulfate is equivalent to 5.585 mg of Iron(III).

EXAMPLE 3

Assay for Citrate from Ferric Citrate 3.1. Material 3.1.1. Mobile Phase

A filtered and degassed mixture of 0.05 M phosphate buffer (adjusted with phosphoric acid to pH 2.2) and methanol (95:5) was prepared.

3.1.2. Preparation of Standard Solution

About 100 mg of citric acid, accurately weighed, was dissolved with 20 mL of water and 5 mL of hydrochloric acid, and was diluted in volume to 50 mL with water and was mixed well. 10.0 mL of the solution was pipetted to a 50 mL volumetric flask and diluted in volume with 0.05% edetate disodium (adjusted with phosphoric acid to pH 2.2) to 50 mL and mixed well. The mixed solution was filtered with a 0.45 um filter. A solution having a known concentration of about 2.0 mg/mL was obtained.

3.1.3. Preparation of Sample Solution

About 100 mg of Ferric Citrate, accurately weighed, was transferred to a 50 mL volumetric flask which contained 20 mL of water and 5 mL of hydrochloric acid and mixed until dissolved, and diluted in volume to 50 mL with water and mixed well. 10.0 mL of the solution was pipetted to a 50 mL volumetric flask and diluted in volume with 0.05% edetate disodium (adjusted with phosphoric acid to pH 2.2) to 50 mL and mixed well. The mixed solution was filtered with a 0.45 um filter.

3.1.4. Chromatographic System

A liquid chromatograph was equipped with a 220-nm detector and a 4.6 mm×15 cm column that contained packing Inertsil 5 ODS-2. The flow rate was about 1.0 mL per minute.

3.2. Procedure (HPLC Assay)

The procedure is that separately injected equal volumes (about 20 uL) of the standard preparation and the sample preparation into the chromatograph, recorded the chromatograms and measured the response for the major peak. The relative standard deviation for replicate injections was not more than 2.0%. The quantity of citric acid in mg per gram in the portion of powder taken by the formula: $R_u/R_s \times W_{st}/W_u \times 1$ 89.11/192.13 was calculated. $W_{st}$ is the weight of citric acid, mg in the standard preparation and $W_u$ is the weight of Ferric Citrate, mg in the sample preparation. $R_u$ and $R_s$ are the peak responses of citric acid from the sample preparation and the standard preparation, respectively.

EXAMPLE 4

Assay the Composition of Ferric Citrate

The composition of commercial ferric citrate varies so much that commercial ferric citrate cannot be used as a drug. Commercial ferric citrates were brought from the Sigma-Aldrich Company, St. Louis, Mo., Fluka Chemie AG, Buchs, Switzerland and Wako Pure Chemical Industries, LTD, Osaka, Japan. Commercial ferric citrates were assayed by ferric titration and a citrate HPLC method. Ferric citrate in the commercial sources are shown in Table I. Ferric citrate was calculated by ferric titration in the 1:1 mole ratio. Ferric citrate was also measured by both the ferric assay result from the titration method and citrate assay result from the HPLC method. The difference of the assay of ferric citrate from the two assays was so great that it was difficult to define the composition of ferric citrate.

TABLE I

The results of Ferric Citrate from the Commercial sources

|   |   | Wako | Sigma1 | Sigma2 | Fulka | Theory |
|---|---|---|---|---|---|---|
| Lot No. |   | SKL1164 | 30H00375 | 20K0950 | 364546/1 | — |
| Emperical Formula |   | $FeC_6H_5O_7 \cdot nH_2O$ | $FeC_6H_5O_7 \cdot nH_2O$ | $FeC_6H_5O_7 \cdot nH_2O$ | $FeC_6H_5O_7 \cdot H_2O$ | $FeC_6H_5O_7 \cdot 3.5H_2O$ |
| Ferric Citrate | Titration | 17.61 | 17.80 | 17.75 | 18.96 | 18.13 |
| Ferric Citrate | HPLC | 65.21 | 62.78 | 66.73 | 67.27 | 60.42 |
| Ferric citrate | Titration | 77.22 | 78.06 | 77.84 | 83.18 | 78.55 |
| Ferric citrate | HPLC + Titration | 82.82 | 80.58 | 84.48 | 86.23 | — |
| Ferric citrate | Difference (Unit: %) | 5.60 | 2.52 | 6.64 | 3.05 | — |

To qualify as pharmaceutical-grade ferric citrate, the content ratio (1:1 molar) of citrate and iron(III) in the crystal is 189.11/55.85=3.39. The four lots of ferric citrate were prepared from the ferric nitrate and citric acid by the solid—solid reaction. The ferric citrate samples were assayed by ferric titration and citrate HPLC method. The results of ferric citrate were shown in Table II. Ferric citrate was calculated by ferric titration in the 1:1 mole ratio. Ferric citrate was also calculated by the addition of ferric assay result and citrate HPLC result. The average difference of the assay of ferric citrate from two assays is 1.48%. This indicates that ferric citrate can be consistently prepared by the solid—solid reaction. The number of hydrates should also be determined in the crystal of ferric citrate, and Tri and half hydrate is determined from the assay results of ferric citrate in the four lots.

TABLE II

The results of Ferric Citrate from the Present Invention

| Lot No. | Emperical Formula | Ferric Titration | Citrate HPLC | Ferric citrate Titration | Ferric Citrate HPLC + Titration | Ferric Citrate Difference (Unit: %) |
|---|---|---|---|---|---|---|
| F920620 | $FeC_6H_5O_7 \cdot 3.5 H_2O$ | 17.72 | 61.56 | 77.72 | 79.28 | 1.56 |
| 911125-2 | $FeC_6H_5O_7 \cdot 3.5 H_2O$ | 17.73 | 63.55 | 77.75 | 81.28 | 3.53 |
| 911115-A | $FeC_6H_5O_7 \cdot 3.5 H_2O$ | 17.84 | 60.42 | 78.23 | 78.26 | 0.03 |
| 911115-B | $FeC_6H_5O_7 \cdot 3.5 H_2O$ | 18.46 | 63.30 | 80.95 | 81.76 | 0.81 |
| Theory | $FeC_6H_5O_7 \cdot 3.5 H_2O$ | 18.13 | 60.42 | 78.55 | — | — |
| — | Average | 17.94 | 62.21 | 78.66 | 80.14 | 1.48 |
| — | RSD | 1.97% | 2.39% | 1.96% | 2.06% | — |

Although the invention has been explained in relation to its preferred embodiment, many other possible modifications and variations can be made without departing from the spirit and scope of the invention as hereinafter claimed.

What is claimed is:

1. A method for preparing ferric citrate comprising:

mixing solid citric acid with a solid ferric salt to form a mixture;

adding alcohol to the mixture; and filtering the mixture to obtain solid ferric citrate.

2. The method as claimed in claim 1, which further comprises drying said solid ferric citrate by heat.

3. The method as claimed in claim 2, wherein said solid ferric citrate is dried at 30° C. to 120° C.

4. The method as claimed in claim 1, which further comprises purifying said solid ferric citrate by mixing with alcohol and filtering the mixture one or more times.

5. The method as claimed in claim 4, which further comprises drying said solid ferric citrate by heat.

6. The method as claimed in claim 5, wherein said solid ferric citrate is dried at 30° C. to 120° C.

7. The method as claimed in claim 1, wherein the ferric salt is ferric chloride, ferric sulfate or ferric nitrite.

8. The method as claimed in claim 1, wherein the obtained ferric citrate is fixed in molecular structure and contains a definite mean number of water molecules.

* * * * *